(12) United States Patent
Li et al.

(10) Patent No.: US 9,131,922 B2
(45) Date of Patent: Sep. 15, 2015

(54) CALIBRATION FOR 3D RECONSTRUCTION OF MEDICAL IMAGES FROM A SEQUENCE OF 2D IMAGES

(71) Applicant: Eigen, Inc., Grass Valley, CA (US)

(72) Inventors: Xin Li, Grass Valley, CA (US); Ramkrishnan Narayanan, Nevada City, CA (US)

(73) Assignee: EIGEN, INC., Grass Valley, CA (US)

( * ) Notice: Subject to any disclaimer, the term of this patent is extended or adjusted under 35 U.S.C. 154(b) by 0 days.

(21) Appl. No.: 13/752,831

(22) Filed: Jan. 29, 2013

(65) Prior Publication Data

US 2014/0213906 A1  Jul. 31, 2014

(51) Int. Cl.
 A61B 8/08 (2006.01)
 A61B 8/12 (2006.01)
 A61B 8/00 (2006.01)

(52) U.S. Cl.
 CPC .......... *A61B 8/5207* (2013.01); *A61B 8/12* (2013.01); *A61B 8/4218* (2013.01); *A61B 8/4245* (2013.01); *A61B 8/4263* (2013.01); *A61B 8/483* (2013.01)

(58) Field of Classification Search
 CPC ........ A61B 8/5207; A61B 8/483; A61B 8/12; A61B 8/5218; A61B 8/4263; A61B 8/4245
 USPC ................................. 600/437–469
 See application file for complete search history.

(56) References Cited

U.S. PATENT DOCUMENTS

| | | | |
|---|---|---|---|
| 3,002,375 A | 10/1961 | Moffat et al. | |
| 3,415,548 A | 12/1968 | Goodman et al. | |
| 5,170,790 A | 12/1992 | Lacoste et al. | |
| 5,230,623 A | 7/1993 | Guthrie et al. | |
| 5,282,472 A | 2/1994 | Companion et al. | |
| 5,398,690 A | 3/1995 | Batten et al. | |
| 5,427,108 A | 6/1995 | Bollinger | |
| 5,487,388 A | 1/1996 | Rello et al. | |
| 5,494,039 A | 2/1996 | Onik et al. | |
| 5,582,173 A * | 12/1996 | Li | 600/443 |
| 5,824,007 A | 10/1998 | Faraz et al. | |
| 5,971,929 A | 10/1999 | Sakamoto et al. | |
| 6,046,727 A | 4/2000 | Rosenberg et al. | |
| 6,171,249 B1 | 1/2001 | Chin et al. | |
| 6,179,262 B1 | 1/2001 | Ellard et al. | |
| 6,246,200 B1 | 6/2001 | Blumenkranz et al. | |
| 6,259,943 B1 * | 7/2001 | Cosman et al. | 600/429 |
| 6,261,234 B1 | 7/2001 | Lin | |
| 6,301,989 B1 | 10/2001 | Brown et al. | |
| 6,325,760 B1 | 12/2001 | Takanori et al. | |

(Continued)

FOREIGN PATENT DOCUMENTS

WO  2007147232  12/2007

*Primary Examiner* — Sanjay Cattungal

(74) *Attorney, Agent, or Firm* — Marsh Fischmann & Breyfogle LLP

(57) ABSTRACT

Provided herein are systems and methods (i.e., utilities) that are directed to correcting misalignments or offsets between a series or sequence of medical images. The utility corrects offsets between a series of medical images obtained where an imaging device (e.g., ultrasound probe) is supported by a positioning mechanism where there is misalignment between an imaging axis or other reference point of the imaging device and the axis of movement of the positioning device. The determination of this offset between these axis allows for calculating a transformation that allows for placing each of the series images into a common frame of reference.

23 Claims, 14 Drawing Sheets

(56) References Cited

U.S. PATENT DOCUMENTS

| | | |
|---|---|---|
| 6,360,027 B1 | 3/2002 | Hossack et al. |
| 6,378,376 B1 | 4/2002 | Derman et al. |
| 6,423,009 B1 | 7/2002 | Downey et al. |
| 6,425,865 B1 | 7/2002 | Salcudean et al. |
| 6,447,447 B1 | 9/2002 | Mitsumori |
| 6,451,027 B1 | 9/2002 | Cooper et al. |
| 6,454,781 B1 | 9/2002 | Witt et al. |
| 6,549,607 B1 * | 4/2003 | Webber .............. 378/8 |
| 6,620,111 B2 | 9/2003 | Stephens et al. |
| 6,752,753 B1 | 6/2004 | Hoskins et al. |
| 6,931,745 B2 | 8/2005 | Granger |
| 7,008,373 B2 | 3/2006 | Stoianovici et al. |
| 7,108,660 B2 | 9/2006 | Stephens et al. |
| 7,189,246 B2 | 3/2007 | Otsuka et al. |
| 7,244,234 B2 | 7/2007 | Ridley et al. |
| 7,255,310 B2 | 8/2007 | Niwa et al. |
| 7,287,310 B2 | 10/2007 | Zuzelo |
| 7,412,776 B2 | 8/2008 | Iikubo et al. |
| 7,472,615 B2 | 1/2009 | Mayeaux |
| 7,475,602 B2 | 1/2009 | Molenaar et al. |
| 7,832,114 B2 | 11/2010 | Suri et al. |
| 7,942,060 B2 | 5/2011 | Suri et al. |
| 2005/0159676 A1 | 7/2005 | Taylor et al. |
| 2008/0004481 A1 | 1/2008 | Bax et al. |
| 2008/0064960 A1 | 3/2008 | Whitmore et al. |
| 2008/0075536 A1 | 3/2008 | Durkheim |
| 2008/0269604 A1 | 10/2008 | Boctor |
| 2009/0145249 A1 | 6/2009 | Dubbeldam et al. |
| 2010/0036245 A1 | 2/2010 | Yu et al. |
| 2010/0142315 A1 * | 6/2010 | Nassiri et al. .............. 367/13 |
| 2012/0207274 A1 * | 8/2012 | Yang et al. .............. 378/62 |

* cited by examiner

2D Image Storage

3D Volume Image

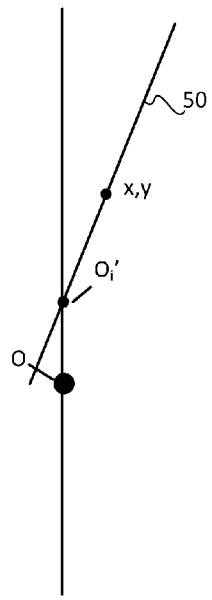 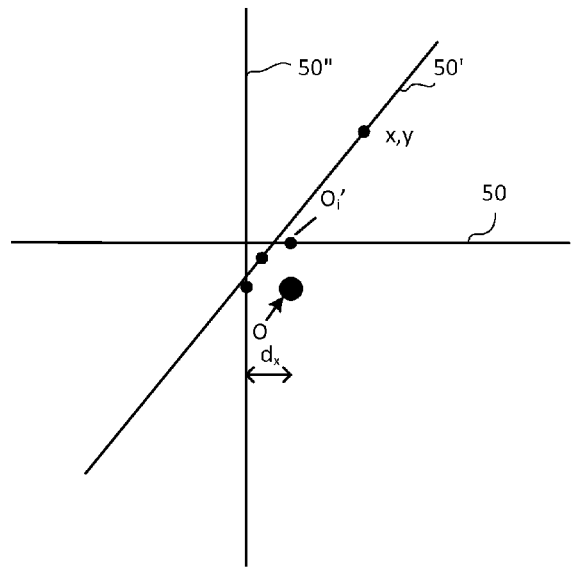
FIGURE 5D  FIGURE 5E
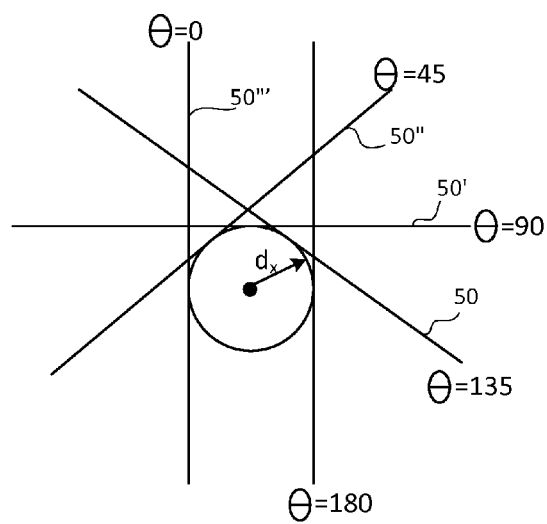
FIGURE 5F (a)          (b)

CALIBRATION FOR 3D RECONSTRUCTION OF MEDICAL IMAGES FROM A SEQUENCE OF 2D IMAGES

FIELD

The presented inventions are directed systems, apparatuses and methods for acquiring a series of images and limiting and/or correcting offset between the images to improve registration thereof.

BACKGROUND

Medical imaging instruments are often utilized by doctors and other medical professionals to conduct non-invasive examinations. That is, medical imaging instruments, including X-ray, magnetic resonance (MR), computed tomography (CT), ultrasound, and various combinations of these instruments/techniques are utilized to provide images of internal patient structure for diagnostic purposes as well as for interventional procedures. Such medical imaging instruments allow examination of internal tissue that is not readily examined during normal visual or tactile examination. Applications include imaging in the areas of mammography, urology and brachytherapy.

Medical imaging devices typically allow for generating 3-D images of internal structures of interest. Such 3-D imaging may improve the accuracy and/or reliability of medical diagnosis. For instance, a medical imaging device may be utilized to generate a 3-D model or map of a patient's prostate such that one or more biopsies may be taken from a desired location of the prostate. For purposes of prostrate imaging, image acquisition and guidance may be provided by a transrectal ultrasound-imaging device (TRUS). In such an application, the ultrasound-imaging device may be inserted into the rectum of a patient to generate an image. Such images may be utilized to take one or more biopsies from a prostate location of interest and/or implant therapy seeds at one or more desired locations in a brachytherapy procedure.

In order to generate 3-D images, many medical imaging devices obtain a plurality of images (e.g., two dimensional images) and combine these images together to form a 3-D image. Traditionally, medical practitioners have manipulated a medical imaging instrument by hand for medical image acquisition and/or treatment. However, in instances where it is desirable to obtain multiple 2-D images for 3-D image generation, manual manipulation of the device may result in the type of unconstrained movement between images that makes registration difficult or impossible. That is, unconstrained (e.g., random) movement of a medical imaging device between the acquisition of individual images makes it more difficult to properly align (e.g., spatially register) the different images for purposes of generating an accurate 3-D image. Accordingly, a number of holding and manipulating/positioning assemblies have been proposed wherein a holder interfaces with an imaging device such as an ultrasound probe. Such a holder is then interconnected to one or more mechanical armatures and/or actuators such that the probe may be controllably positioned, advanced and/or rotated. In such systems, the position of the probe is known and movement of the probe (e.g., rotational, linear, etc.) is typically limited to a single degree of freedom. In this regard, the offset (e.g., angular or linear) between images is known. Accordingly, registration of such images is simplified.

SUMMARY

Provided herein are systems and methods (i.e., utilities) that are directed to correcting misalignments or offsets between a series or sequence of medical images. Once the offsets or misalignments between the series of medical images is corrected, the series of medical images may be reconstructed into a three dimensional image. In this regard, the correction of the offsets between the images registers these images into a common frame of reference such that they may be reconstructed into a three dimensional image. Accordingly, in order to correct the offsets, it is necessary to determine the transformation between the images. In this regard, the inventors have recognized that one source of offsets between a series of medical images obtained where an imaging device (e.g., ultrasound probe) is supported by a positioning mechanism or device, is the misalignment between the imaging axis or other reference point of the imaging device and the axis of movement of the positioning device. For instance, in the case of an ultrasound imaging device (e.g., two dimensional ultrasound device) an image plane of the ultrasound device may be misaligned with the movement axis of the positioning device. The determination of this offset between these axes allows for calculating a transformation that allows for placing each of the series images into a common frame of reference.

According to a first aspect, the utility is provided where at least first and second images are obtained from an ultrasound imaging device while the ultrasound imaging device is supported by a positioning device. More specifically, the first and second images are obtained while the positioning device supports the ultrasound imaging device in first and second positions. The positioning device is operative to support the ultrasound imaging device in the first and second positions while limiting movement of the ultrasound imaging device to a single axis. Such a single axis may be a linear axis of movement or a rotational axis of movement. The first and second images are analyzed, automatically or manually, to identify and align a common object therein. In this regard, a first distance between the object and a known reference point (e.g., imaging axis) is identified in the first image. The second image is likewise analyzed to identify a second distance between the common object and the reference point. The distances between the common object in the first and second images and the known reference point are utilized to calculate a transformation that aligns the common object from both images. This transformation defines a calibration of offsets between the reference point of the ultrasound images and the axis of movement of the positioning mechanism.

Once the transformation is calculated for the images, such a transformation may be utilized with subsequently acquired images in order to place those images in a common frame of reference. That is, after calculating a transformation, the utility may allow for acquiring a sequence of additional two dimensional images of an anatomical object using the ultrasound device as supported by the positioning mechanism. Again these two dimensional images may be acquired at multiple different positions about the axis of movement of the positioning device. Once transformed utilizing the calculated transformation, these images are registered to a common frame of reference and may be reconstructed to generate a 3D image of the anatomical object.

In one arrangement, the acquisition of the images is obtained through the acquisition of first and second images (e.g., image pairs) where these images are obtained about a rotational axis. In this arrangement, the first and second images of each pair of images are acquired at 180 degrees apart. In this regard, each of these pairs of images, images the same anatomical structure. That is, the images are mirror images. Accordingly, a common object in each of these images should be a common distance away from, for example, an imaging axis of the imaging device. Further, it will be appreciated that multiple pairs of 180 degree spaced images may be utilized to calculate a more robust transformation.

In a further arrangement, during the subsequent stacking of the images that are corrected utilizing the calculated transformation, each image may be registered to an adjacent image in order to account for movement of the anatomical object within each image.

In a further arrangement, the images may be preprocessed to remove speckle and/or shadow to improve registration between images.

BRIEF DESCRIPTION OF THE DRAWINGS

FIGS. 5D-5F illustrate out-of-plane offset.

DETAILED DESCRIPTION

Reference will now be made to the accompanying drawings, which assist in illustrating the various pertinent features of the present disclosure. Although the present disclosure is described primarily in conjunction with transrectal ultrasound imaging of a prostate, it will be expressly understood that aspects of the presented inventions are applicable to other medical imaging applications and other medical imaging techniques. That is, the inventions are applicable to a broad range of imaging modalities, including MRI, CT, and PET as applied to any of variety of anatomical structures. In this regard, the following description is presented for purposes of illustration and description. Furthermore, the description is not intended to limit the invention to the form disclosed herein. Consequently, variations and modifications commensurate with the following teachings, and skill and knowledge of the relevant art, are within the scope of the present invention.

Disclosed herein are systems and methods that facilitate registration of a sequence of 2D images, which may generate a 3D image. In various embodiments, the systems and methods allow for accounting for offsets that may exist between successive images to improve accuracy of the resulting registered image(s) (e.g., 3D image).

Figure 1:
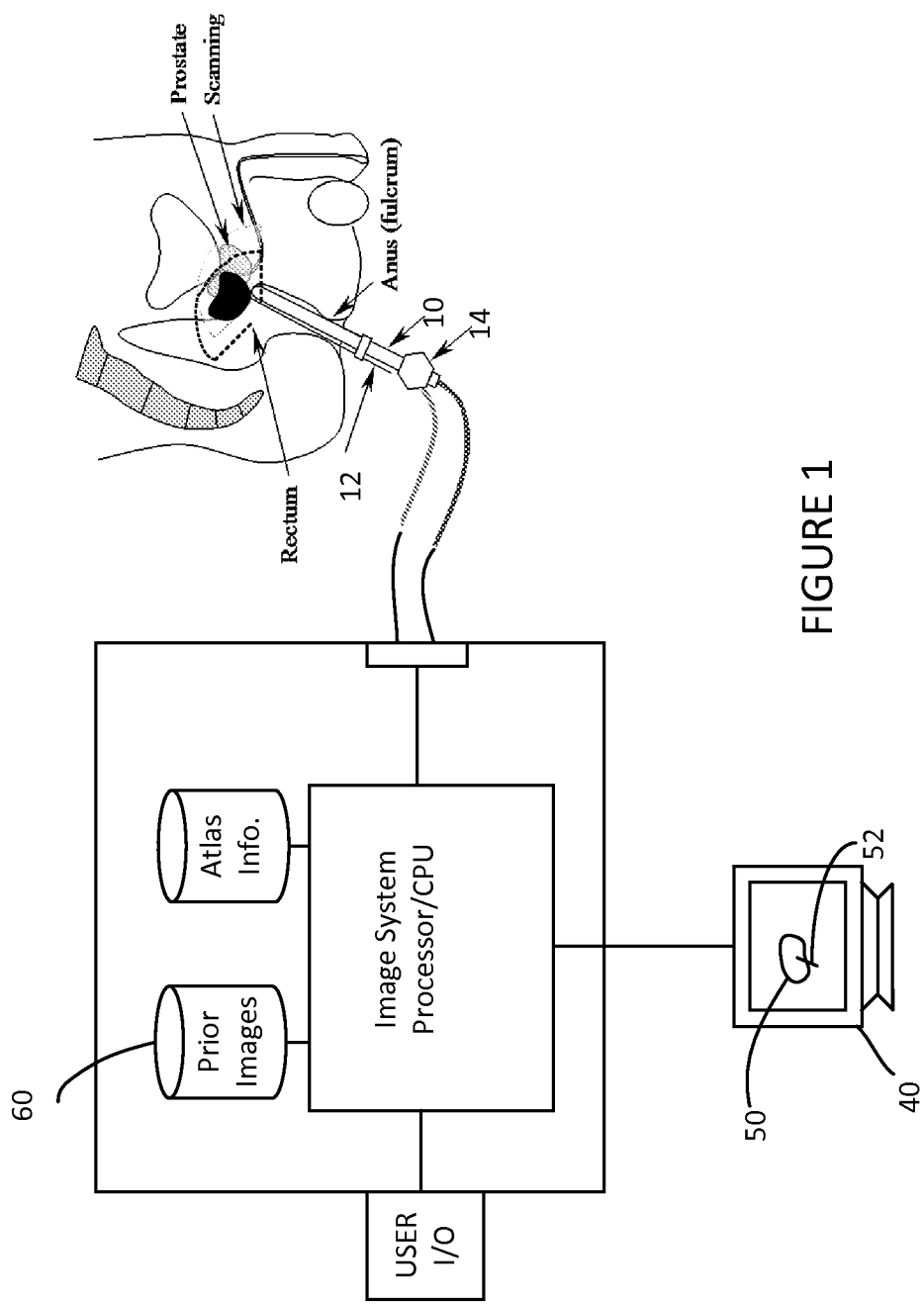
FIG. 1 shows a cross-sectional view of a trans-rectal ultrasound imaging system as applied to perform prostate imaging.
Figure 3A:
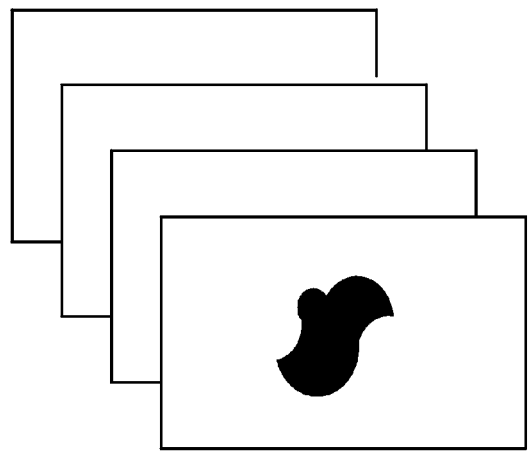
FIG. 3A illustrates two-dimensional images generated by the TRUS of FIG. 1.
Figure 3B:
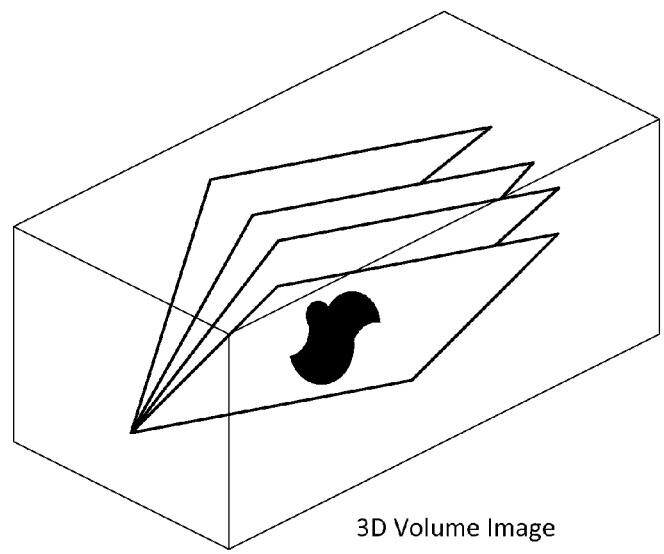
FIG. 3B illustrates a 3-D volume image generated from the two dimensional images of FIG. 3A.

FIG. 1 illustrates a transrectal ultrasound (TRUS) probe 10 being utilized to obtain a plurality of two-dimensional ultrasound images of a prostate of a patient. In such an arrangement, a user may rotate the acquisition end of the ultrasound probe 10 over an area of interest. Accordingly, the probe 10 may acquire plurality of individual images while being rotated over the area of interest. Each of these individual images may be represented as a two-dimensional image. See FIG. 3A. These two-dimensional images may be combined to generate a 3-D image. See FIG. 3B.

In an attempt to reduce offset between successive images, the probe may be interfaced with a positioning device or tracker assembly 100 such that a supported probe may be rotated about a fixed axis or advanced along a linear path. See FIG. 2. One exemplary tracker assembly is set forth in International Application Number PCT/CA2007/001076, entitled: "Apparatus for Guiding a Medical Tool". Another is set forth in U.S. application Ser. No. 11/850,482, entitled: "Tracker Holder Assembly", the contents of both of which are fully incorporated herein by reference. In this regard, the multiple images may be obtained from the supported probe 10 in different angular or linear positions for 3-D image generation. As the probe 10 is securely supported by the tracker assembly 100, there is limited probe movement, other than about the fixed axis of rotation, between successive images. The known constrained movement between successive images allow the images to be more readily are registered together.

Figure 2:
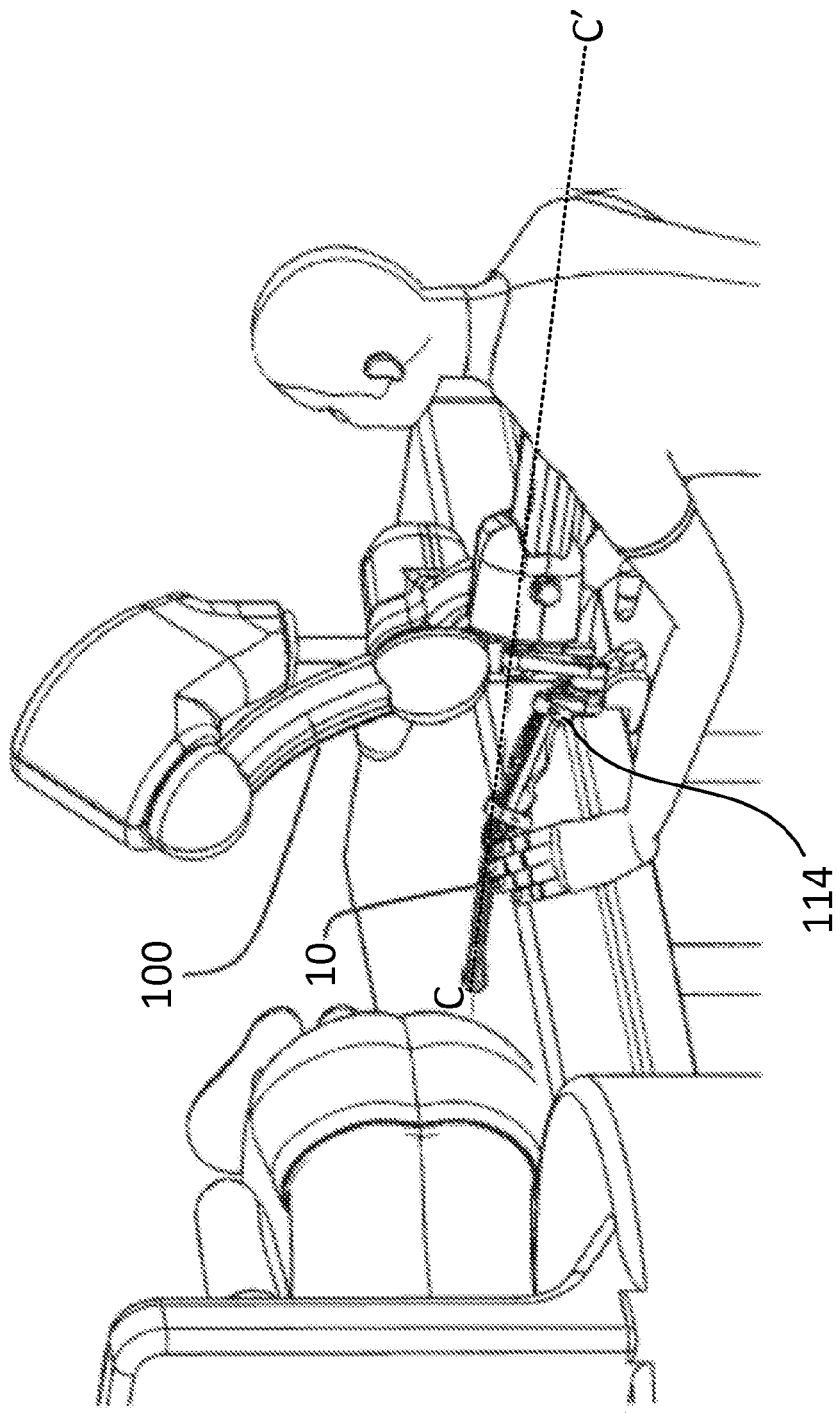
FIG. 2 illustrates use of a positioning/tracking device to position an ultrasound imaging device to perform prostate imaging.

As shown in FIGS. 1 and 2, the illustrated probe 10 is an end-fire transducer that has a scanning area of a fan shape emanating from the front end of the probe (shown as a dotted outline). It will be appreciated that other probes may be utilized (e.g., side fire etc.). A handle of the probe is held by a cradle assembly 114 that connects to an armature of the tracker assembly 100. The tracker assembly includes a set of position sensors which are connected to the computer 20 of the imaging system 30 via an analog to digital converter. Hence, the computer 20 has real-time information of the location and orientation of the probe 10 in reference to a unified Cartesian (x, y, z) coordinate system.

With the dimensions of the probe 10 taken into the calculations, the 3D position of each 2D image plane obtained by the probe and its orientation is known. The ultrasound probe 10 sends signal to the image guidance system 30, which may be connected to the same computer (e.g., via a video image grabber) as the output of the armature position sensors. In the present embodiment, this computer is integrated into the imaging system 30. The computer 20 therefore has real-time 2D and/or 3D images of the scanning area in memory 22. The image coordinate system and the arm coordinate system may be unified by a transformation. Using the acquired 2D images, a prostate surface 50 (e.g., 3D model of the organ) may be simulated and displayed on a display screen 40 with their coordinates displayed in real-time. A biopsy needle 52 or other guided instrument may also be modeled on the display, which has a coordinate system so the doctor has the knowledge of the locations of the instrument and the internal structure of interest.

The computer system runs application software and computer programs which can be used to control the system components, provide user interface, and provide the features of the imaging system including the calibration functions described herein. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software, as provided on the computer-readable media or downloaded from electronic links, represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

To improve registration of images, it is desirable that relative movement (e.g., wobble) between the probe 10 and an imaged area be minimized (i.e., other than rotational movement of the probe about a fixed axis for image acquisition). As noted, to minimize such relative movement, the probe 10 interfaces with a positioning or tracker assembly 100 (see FIG. 2), which limits movement of the probe 10 to a single degree of freedom (e.g., rotation, linear advancement, etc) as well as providing location information (e.g., frame of reference information) for use with an acquired image.

Figure 4:
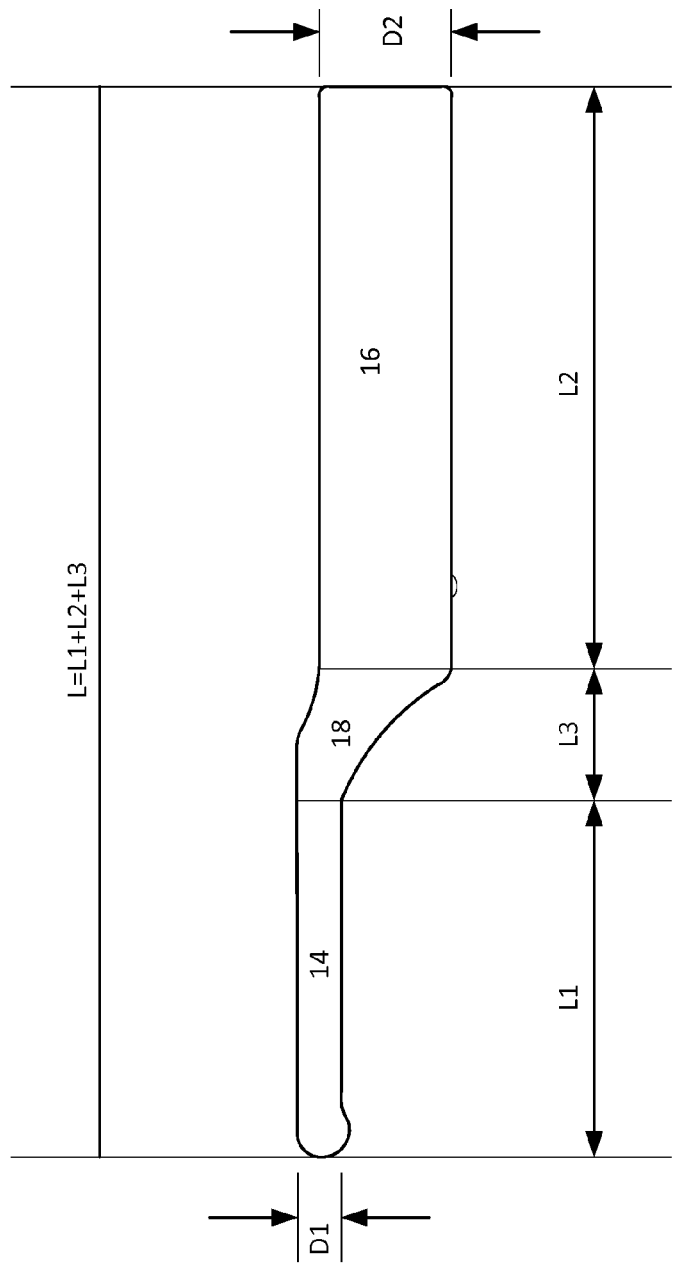
FIG. 4 illustrates an exemplary ultrasound probe.

In order to utilize a probe 10 with the tracking assembly as illustrated in FIG. 2, it is necessary to secure the probe 10 to the assembly. That is, an interface between the probe and tracking assembly is required. Complicating the interfacing of an ultrasound probe with a positioning/tracking assembly is the fact that probes made by different probe manufacturers have different dimensions. For instance, FIG. 4 illustrates an exemplary TRUS probe 10. As shown, the probe includes an insertion end/acquisition end 14 having a first length $L_1$ (i.e., insertion length) and a first diameter $D_1$ (i.e., insertion diameter). In the illustrated embodiment, the insertion end along the long axis of $L_1$ defines a desired axis of rotation (i.e., acquisition axis). The probe 10 also includes a handle 16 having a second length $L_2$ (i.e., a holding length) and a second diameter $D_2$. Further, the probe may have a transition 18 between the insertion end 14 and handle 16.

The dimensions (e.g., lengths and/or diameters) of any or all of these components 14, 16 and 18 may vary between probes of different manufactures. Further, these components may be tapered and/or set at an angle to one another. Therefore, to interface different probes to a common positioning device typically requires individual probe interfaces or "cradles". In many instances, such cradles are specially designed to accommodate a particular probe. One example of such a cradle is provided in U.S. Patent Publication No. 2009/0227874, the entire contents of which are incorporated herein by reference. In other arrangements, universal holders/cradles are utilized that attempt to interface with a variety of probes.

The tracker assembly tracks the coordinates of an instrument (i.e., probe) in 3D space. Furthermore, the tracker assembly 100 also supports the probe and provides orientation of the probe for an interconnected imaging system. The tracker assembly also measures the rotation of the probe around a rotational axis or along a linear axis. That is, during image acquisition, it is typical to move an acquisition end of the ultrasound probe relative to a tissue area of interest (e.g., the prostrate). Once so positioned, the probe may be rotated or advanced while a plurality of 2-D images are obtained for use in generating a 3-D image. The images may be acquired at equal angular or linear offsets in order to provide an improved 3-D image. To allow equal angular offsets, the probe rotation may be motorized or utilize a ratchet and pawl arrangement such as set forth in U.S. patent application Ser. No. 11/691,150, as incorporated above. In any case, the tracker assembly provides an output that identifies the position of the probe which may be utilized in conjunction with an image acquired by the probe in that position to generate a 3D image.

Irrespective of the type of holder or tracker utilized, it is necessary that the holder position the probe in a desired orientation. For instance, for a probe designed to be rotated the insertion axis of the probe 10 typically needs to be aligned with the rotational axis C-C' of the tracker assembly 100 to provide a series of images having a common frame of reference. In this arrangement, the cradle 114 is designed to support the acquisition/insertion end of the probe 10 in alignment with the rotational axis C-C' of the tracker assembly 100. While simple in theory, in practice alignment of these axes is not exact. That is, owing to mechanical tolerances and/or residual stresses, the acquisition axis of the probe is typically slightly misaligned with the rotational axis of the tracker assembly. The same is generally true in other tracker assemblies (e.g., linear systems). Stated otherwise, residual misalignments remain between a tracker assembly and an image plane of an imaging device connected to the tracker assembly.

In many applications, the magnitude of such residual misalignment is not of great importance. However, in applications where a series of 2D images are reconstructed into a 3D image, any residual or other misalignment is reflected in poor 3D reconstruction. That is, different images that include a common structure of interest (e.g., lesion) may not properly align. In some estimations, residual misalignments result in offsets as large as 10 mm between common structures of interests in different images even instate-of-the-art imaging and tracking systems. In this regard, the reconstruction of the structure of interest may not be well defined.

While attempts continue to provide improved physical alignment and physical isolation between an imaging device and a positioning device, the present inventions are based in part on the realization that offsets between, for instance, the direction of movement of a tracker assembly (e.g., linear, rotational) and an imaging plane of an imaging device may be accounted for after image acquisition. That is, the images may be processed after acquisition to account for residual offsets.

Figure 5A:
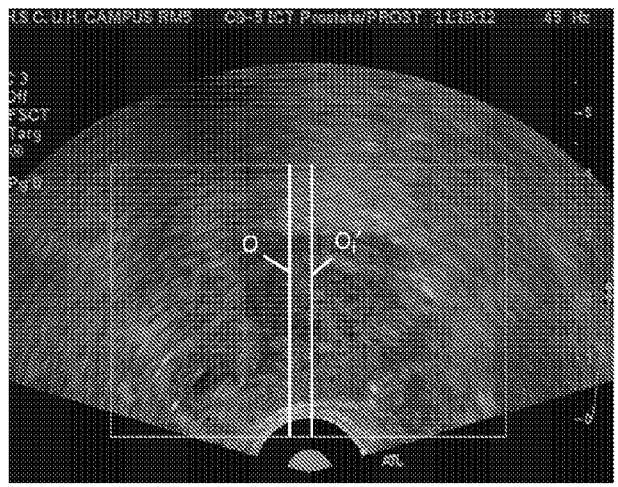
FIG. 5A illustrates in-plane translation offset
Figure 5B:
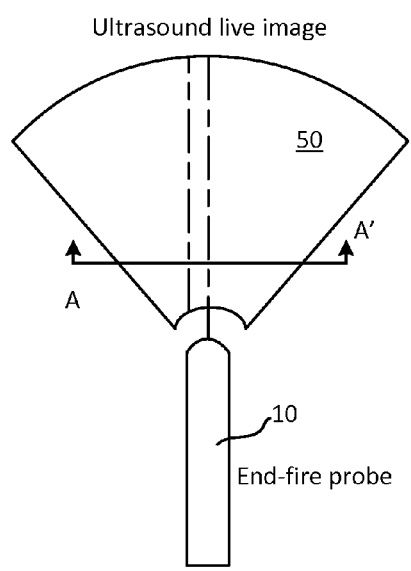
FIG. 5B shows a typical ultrasound imaging plane acquired by an end-fired transducer probe.
Figure 5C:
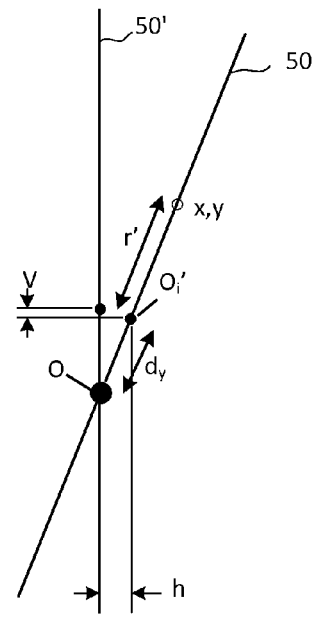
FIG. 5C shows a cross-sectional view (as seen from behind an end-fired probe) of in-plane translation offset.
Figure 6:
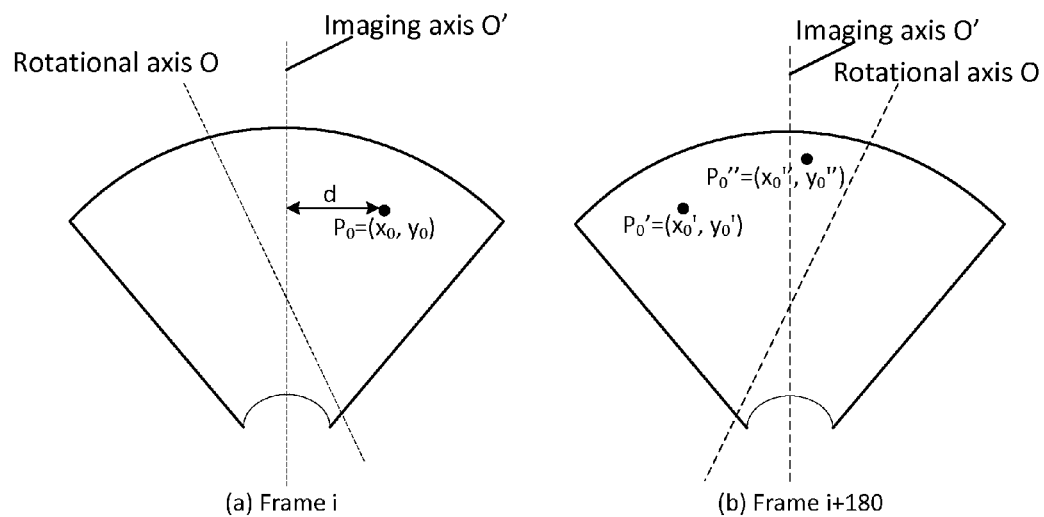
FIG. 6 illustrates the imaging plane with in-plane rotation and translation offset.

FIG. 5A-5F illustrate two different offsets that can exist between an actual axis of rotation O (i.e., the rotational axis of a tracker assembly) and the imaging axis O' of an ultrasound probe. In the illustrated embodiments, the offsets are described in conjunction with an end-fire probe 10 that generates a single image plane 50 emanating from the front end of the probe 10. See FIG. 5B. It will be appreciated that other probes may be utilized (e.g., side fire etc.). The in plane misalignment if referred to as a combination of in plane translation offset and rotation offset as is shown in FIG. 6. FIG. 5A and FIG. 5C illustrated a special situation of in plane misalignment where only in plane translation offset exists. As illustrated in FIGS. 5A and 5B, the imaging axis O' of the probe 10 is offset from the rotational axis O of the tracker assembly. However, the image plane 50 of the probe contains the axis O of the tracker assembly. This in-plane translation offset is illustrated in FIG. 5C, which shows the image plane 50 from the perspective of cross-section A-A' of FIG. 5B. In this cross-sectional view, the image plane 50 is shown as a line that passes through the imaging axis O' of the probe as well as the imaging axis O of the tracker assembly. As illustrated, the imaging axis O' is offset a distance $d_y$ from the rotational axis. The result of this offset is that a point in the image (x,y) that is a distance r' from the imaging axis is displaced an additional distance $d_y$ from the rotational axis, which is typically reference point utilized to register successive images together. Further, as the probe is rotated around the rotational axis O, subsequent images (e.g., image plane 50') are each offset a distance $d_y$ from the rotational axis (i.e., at different angular locations) and are offset (in translation and rotation) from the location of the previous image either or both vertically 'v' and/or horizontally 'h'. In the absence of offset correction, these images 50, 50', 50" etc., are not registered in common frame of reference.

FIGS. 5D-5F, the imaging axis O' is offset from the rotational axis O of the tracker and where the image plane 50 of the probe does not pass through the rotational axis O. This is referred to as out-of-plane misalignment. In this out-of-plane misalignment offset situation, the image plane 50 of the probe processes around the rotational axis O of the tracker. This results in acquiring a series of images 50-50'''(see FIG. 5F) whose planes form a circle around the axis of rotation O. In this situation, no imaging information is acquired for the area (i.e., circle) within the offset $d_x$ between the rotational axis O and the imaging axis O'. That is, the region inside of the circle having the radius $d_x$ is never imaged. Likewise, the successive images 50-50''' are each offset from one another and, absent correction, are not registered in a common frame of reference.

The misalignment caused by in plane translation and rotation of an imaging axis with rotational axis is illustrated in FIG. 6. As shown in the left panel of FIG. 6, which illustrates a first image frame (i), a point $P_0$ in the image is located a distance 'd' from the imaging axis O' of an ultrasound probe. If the imaging axis O' were properly aligned with the rotational axis O of the tracker assembly, this point $P_0$' would be expected to be an equal distance 'd'' from the imaging axis O' when the imaging plane 50 is rotated 180° as shown in the right panel of FIG. 6, which illustrates a subsequent imaging frame (i+180). That is, the point $P_0$ would be shown in the image plane on the opposite side of the imaging axis O' and would be located an equal distance from the imaging axis. However, when the imaging axis O' and rotational axis O are misaligned, the actual location of the initial point $P_0$ is located at a different location. By way of example, the location in the subsequent frame 'i+180' of $P_0$ is at $P_0$'' as shown by the meshed dot. Accordingly, in order to better register these two images to a common frame of reference, it is necessary to map $P_0$' back to its proper location $P_0$''. In order to map the points (e.g., each pixel of the image) back to its proper location, it is necessary to determine a transformation between the images. As more fully discussed herein, the presented systems and methods use a sequence of phantom images, each pair acquired at angular separation of 180 degrees and registers corresponding image pairs to compute the deviation from designed axis.

For misalignment calibration, an ultrasound phantom is imaged such that a number of image frames and their corresponding images that are angularly separated by 180 degrees are acquired as the transducer is rotated about its expected imaging axis. As a result, image pairs at angular separation of 180 degrees should be mirror images of each other about the imaging axis, if the imaging axis is correct. In case of misalignments, artifacts such as FIG. 6 will be seen. In such cases, sequence of such image pairs are acquired and image registration of identified points, as further described herein, is used to compute and correct for the misalignment. Once the transformation between the image pairs is known, the offsets between the images may be corrected.

Figure 7:
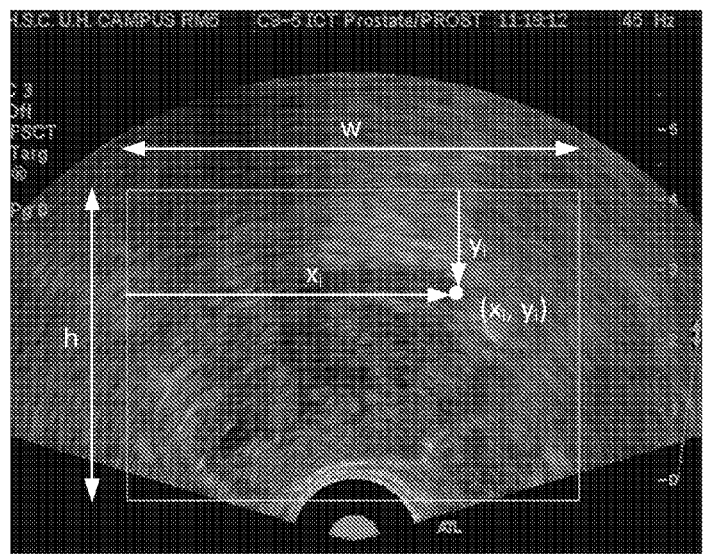
FIG. 7 illustrates the ROI within the image for 3D reconstruction.

In uncorrected image acquisition and "on-the-fly" reconstruction method, a sequence of rotationally separated 2-D slices is acquired as a series of 2-D images. Each 2-D image is stored as a 1-dimensional array of size $(n_x \times n_y)$ such that intensity at a pixel location (x,y) is stored at index $x+(n_x-1)y$. The correction (i.e. rotation and translation of the transformation), is applied to each frame after acquisition and before saving it as a volume series. The sequence is stored as a one dimensional structure such that for i-th slice, a point $(x_i, y_i)$ is stored at index $(i-1)\cdot(w*h)+y_i*w$; where w represents the width of a region of interest (ROI) in a an image and h represents the height of the ROI. $x_i$ and $y_i$ represent the horizontal (left to right) and vertical (top to bottom) coordinates in 2-D frame of reference of the ROI, respectively. This is illustrated in FIG. 7 where the ROI is illustrated as a rectangle within the image.

The rotation angle and the translation both in x and y direction are calculated using the transformation described herein. The original coordinates are first translated and then the rotation is performed about the center of the 2D image Given the coordinates $x_i$ and $y_i$ in a 2D frame, the new transformed coordinates can be calculated as:

$$x_2=(x_i-tx-\text{ROIWidth}/2)*\cos(\theta)-(y_i-ty-\text{ROIHeight}/2)*\sin(\theta)+\text{ROIWidth}/2$$

$$y_2=(y_i-ty-\text{ROIHeight}/2)*\cos(\theta)+(x_i-tx-\text{ROIWidth}/2)*\sin(\theta)+\text{ROIHeight}/2$$

where, $x_2$ and $y_2$ are the transformed coordinates after applying the correction $x_i$ and $y_i$ are the x and y coordinates of the initial acquired 2D frame tx, and ty are the translation parameters in x and y directions, respectively ROIWidth is the width of the acquired 2D frame ROIHeight is the height of the acquired 2D frame This transformation allows for mapping points (e.g., pixels) of different images back to a common frame of reference. However, this relies on two assumptions:

1. The scan is performed such that there is only one motion—rotational motion about the imaging axis.

2. There is no lateral or axial shift or tilt, i.e., the imaging axis and rotational axis are perfectly aligned and coincide. Based on these assumptions, the correspondence between a point (x, y, z) and the rotational slice i does not change with the depth parameter z. If index of a pixel (x, y, z) is represented as sum of two indexes I(z, i) and J(x, y), then a reverse map can be created in advance for computing index J for all (x, y) locations. This is possible since as per the assumptions of no tilt, J is independent of z. For a given z, the index I representing the beginning of the rotational 2-D frame corresponding to the screen coordinates (x,y), can be computed as:

$$I=(i-1)\cdot w\cdot h+(z-1)\cdot w, \quad (1)$$

where z is measured from front face of a 3D reconstructed image cube and $$i = \text{floor}\left(\frac{\theta}{\Delta\theta}\right); \quad (2)$$

$$\theta = \tan^{-1}\left(\frac{y - \frac{w}{2}}{x - \frac{w}{2}}\right) \quad (3)$$

and, $\Delta\theta$ represents the angular separation between two consecutive rotational slices. I provides the 1-dimensional index of the central pixel of current rotational slice I and index J needs to be added to it to get the index corresponding to the screen coordinate (x,y). For a given screen coordinate (x, y), J is given by:

$$J = \frac{w}{2} \pm r \quad (4)$$

Where, for a given point (x, y) on screen, $$r = \sqrt{\left(x - \frac{w}{2}\right)^2 + \left(y - \frac{w}{2}\right)^2} \quad (5)$$

and ± sign is determined by the check whether the point (x, y) lies after w/2 or before.

The assumptions made do not hold valid for a misaligned TRUS probe. Consider a case where the imaging plane is axially shifted with respect to the rotational plane. In such a case, a scenario similar to FIG. 5C (i.e., when there is an in-plane shift) occurs where intensity values are computed and assigned to the incorrect pixel locations. FIG. 5C shows true coordinate correspondence pertaining to in-plane axial misalignment and FIG. 5D shown an incorrectly computed index. As shown in these images, O represents the true axis of rotation and O' represents the imaging axis and the correct x, y location corresponds to a fixed distance 'r' from the imaging axis O'. In this case, the mapping should return the index J corresponding to corrected value of r'=r–dy. For this case, the angle does not change and the eq. 3 can be used to compute the angle and index I. However, for a point (x,y) in screen coordinate system, the equivalent index will be at J–$d_y$.

In the case of out-of-plane misalignment as shown in FIGS. 5E and 5F, lateral shift of the imaging axis O' causes the center of imaging axis O' to precess about the axis of rotation O. In this situation, not all the pixels in screen coordinates are scanned due to precession of the ultrasound transducer about the axis of rotation. In FIG. 5F, the black dot at center represents the imaging axis O and $d_x$ represents the lateral shift to the right side of imaging axis O' at angle $\theta$=0. As the transducer is rotated, the imaging plane rotates about the imaging center and the center of imaging plane follows a circular path about this center. At angle of 90 degrees, the imaging axis is located at a vertical distance of $d_x$ from the rotational axis with image plane being horizontal. At 180 degrees, the imaging plane is vertical, but at a horizontal distance of $d_x$ to the right of imaging axis. The figure shows that even with a full 360 degrees rotation, the region contained inside the circle of radius $d_x$ about the imaging axis is never scanned. This is not critical if the ROI of internal tissue being scanned is not within the circle. However, the acquired images are offset from one another and require correction for proper registration.

Where $d_x$ represents the axial misalignment in lateral direction, then, a number of cases exist for different values of uncorrected r and $\theta$. The different cases are discussed below.

Case 1: 0<$\theta$<90
a) r cos $\theta$>$d_x$
FIG. 8A shows this case, where the corrected value of $\theta$ is varied from 0 from 90 degrees. In uncorrected screen coordinates, the uncorrected angle $\theta$ shall lie between 0 degrees and $\cos^{-1}(d_x/r)$. Then, $$\theta_c = 90 + \theta - \sin^{-1}\left(\frac{r'}{r}\right)$$

and $$r' = \sqrt{r^2 - d_x^2}.$$

b) r cos $\theta$=$d_x$
When r=$d_x$/cos $\theta$, $\theta_c$=90 degrees and r'=$\sqrt{r^2 - d_x^2}$=r sin 0.
c) $d_x \le r < d_x/\cos\theta$
This case is shown in FIG. 8B. In this case, the corrected angle $$\theta_c = 90 + \theta - \cos^{-1}\left(\frac{r'}{r}\right)$$

and $$r' = \sqrt{r^2 - d_x^2}.$$

d) r<$d_x$
In this case, the (x,y) location does not map back to any scanned point or index in the raw image array.

Figure 8:
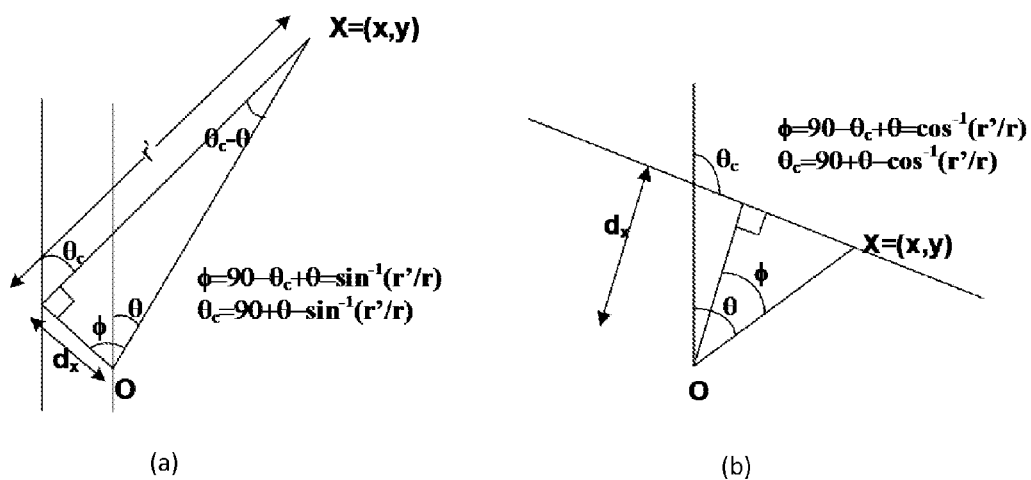
FIG. 8 illustrates the correction for lateral shift.

Case 2: 90<$\theta$<180
The slice index i is then computed based on corrected angle $\theta_c$, i.e., i=floor ($\theta_c/\Delta\theta$) and r' is used instead of r to compute the corresponding element in that slice. FIG. 5F represents a case where r>$d_x$ and $\theta$>0. There are various possible scenarios:
2.1 r=$d_x$
2.2 r<$d_x$. In this case, there is no frame that corresponds to the current pixel location on screen, as can be seen in FIG. 8.

Figure 9:
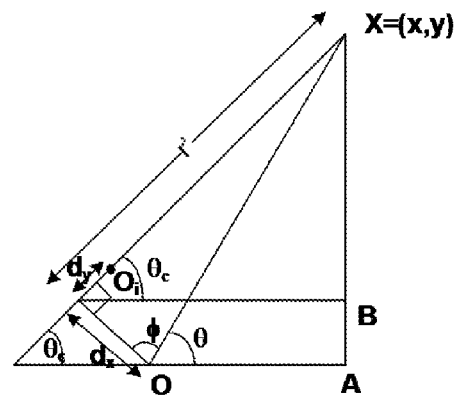
FIG. 9 illustrates the correction for combined in-plane and lateral shift.

When, both in-plane and lateral shifts are present in the system, then the combined effect in a plane for constant z can be represented by FIG. 9 and computations can be made as follows:

$$OX = r = \sqrt{\left(x - \frac{w}{2}\right)^2 + \left(y - \frac{w}{2}\right)^2}$$

$$r' = \sqrt{r^2 + d_x^2} - d_y$$

$$\phi = \theta_c + 90 - \theta = \tan^{-1}\left(\frac{r'}{d_x}\right)$$

$$\Rightarrow \theta_c = \tan^{-1}\left(\frac{r'}{d_x}\right) + \theta - 90$$

Figure 10:
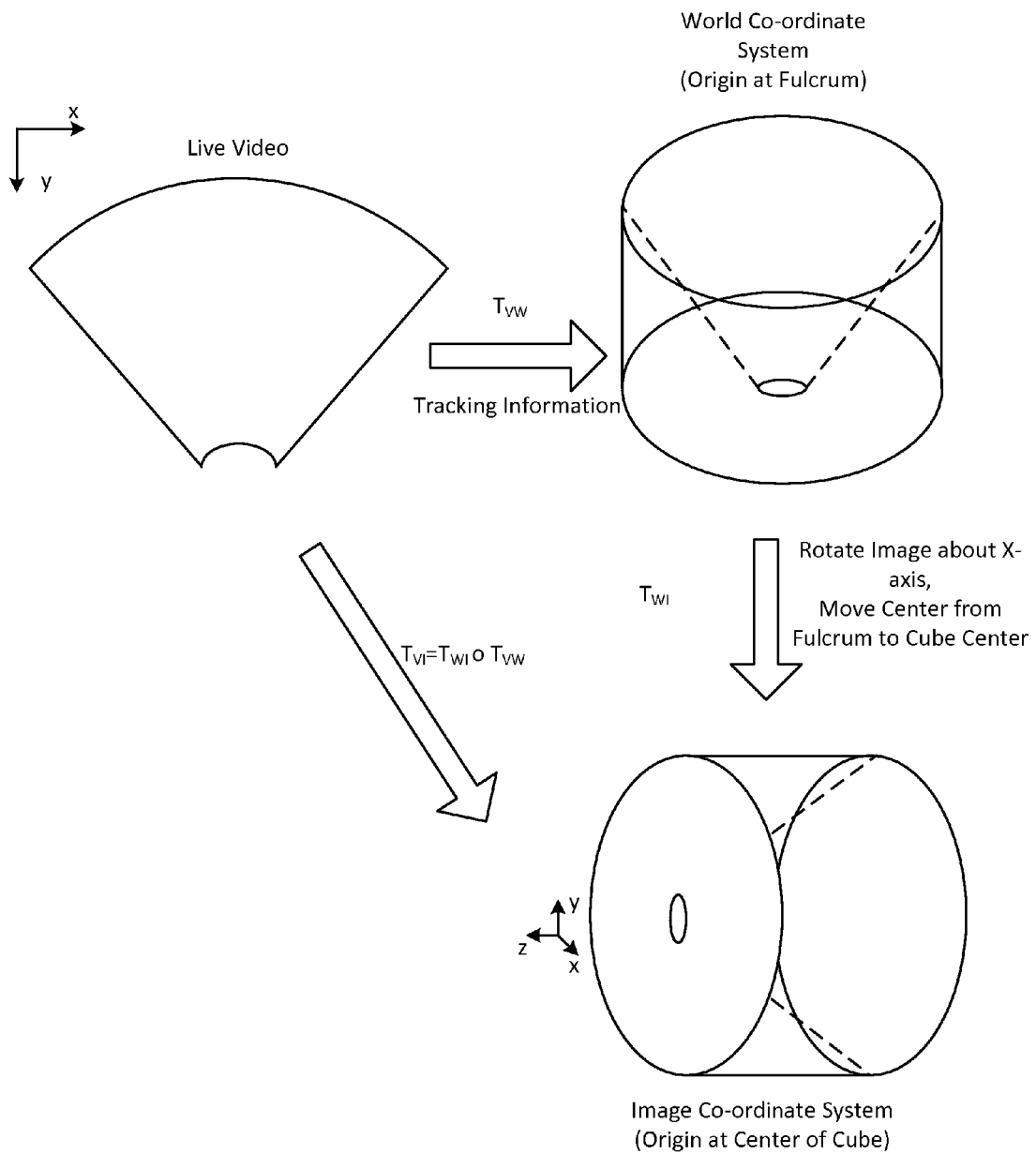
FIG. 10 illustrates the different coordinate systems used in a 3-D imaging system.

FIG. 10 shows the different coordinate systems used in a 3-D imaging system in accordance with the presented inventions. The 2-D coordinate system of the ultrasound live scan is called Video Coordinate System. The tracking information is used to dynamically generate a transformation matrix $T_{VW}$ that transforms the live video into a frame of reference called World Coordinate System. The World Coordinate System is further converted into another coordinate system called Image Coordinate System using a fixed transformation $T_{WI}$ to be compatible with native frame of reference of VTK. The World Coordinate System has origin at the fulcrum which is a pivot point in 3D space that is always on the probe axis with any tracker orientation, and the depth represented as "Y" dimension in right hand coordinate system. The transformation TWI rotates the coordinate system of World Coordinate System by rotating it about x-axis by 90 degrees and translating the origin to center of the scanned cube. This defines the Image Coordinate System. This transformation as described in relation to FIG. 10, does not account for the offsets between individual images caused by misalignment. In order to account for such offsets, an additional transformation must be computed to align the images.

Figure 11:
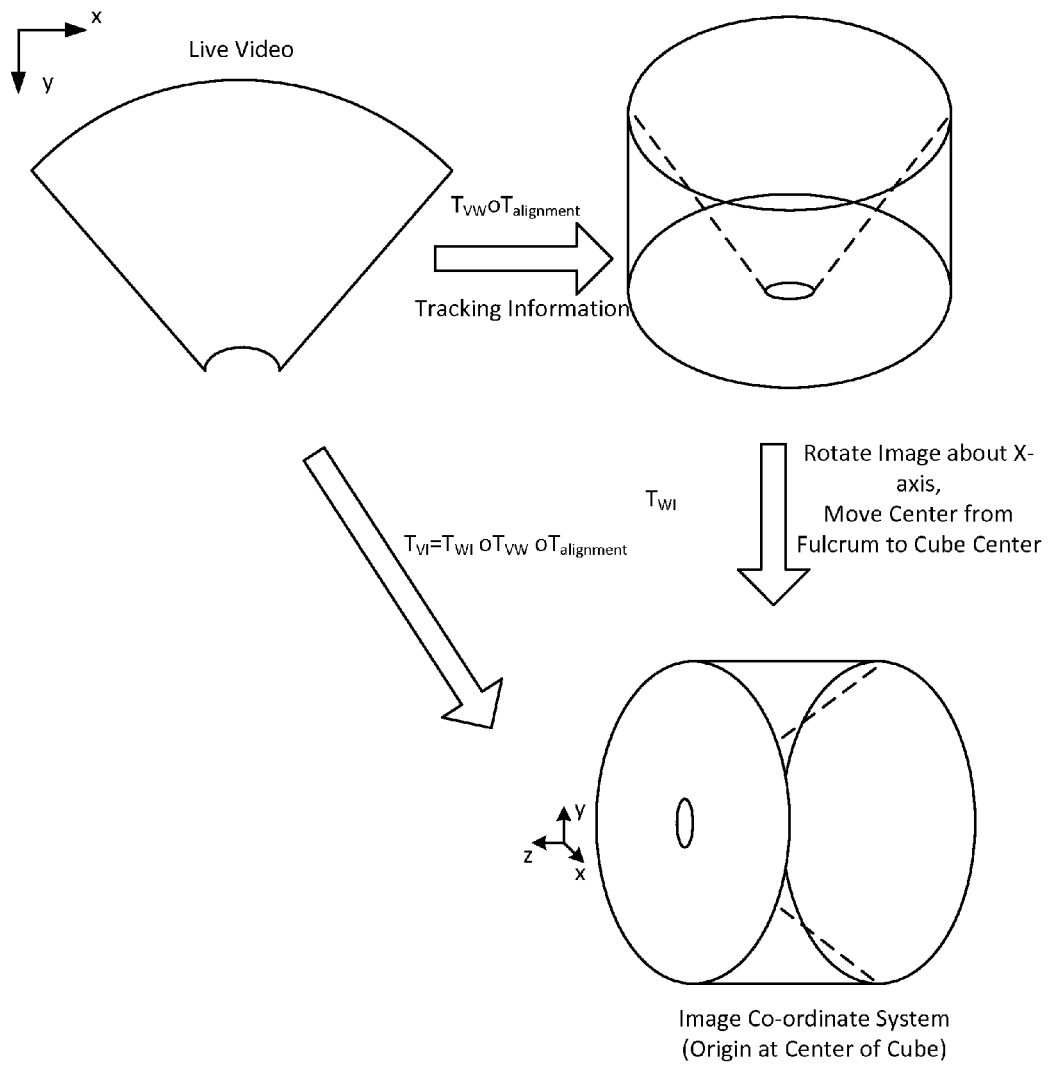
FIG. 11 illustrates the different coordinate systems with misalignment transformation.
Figure 12:
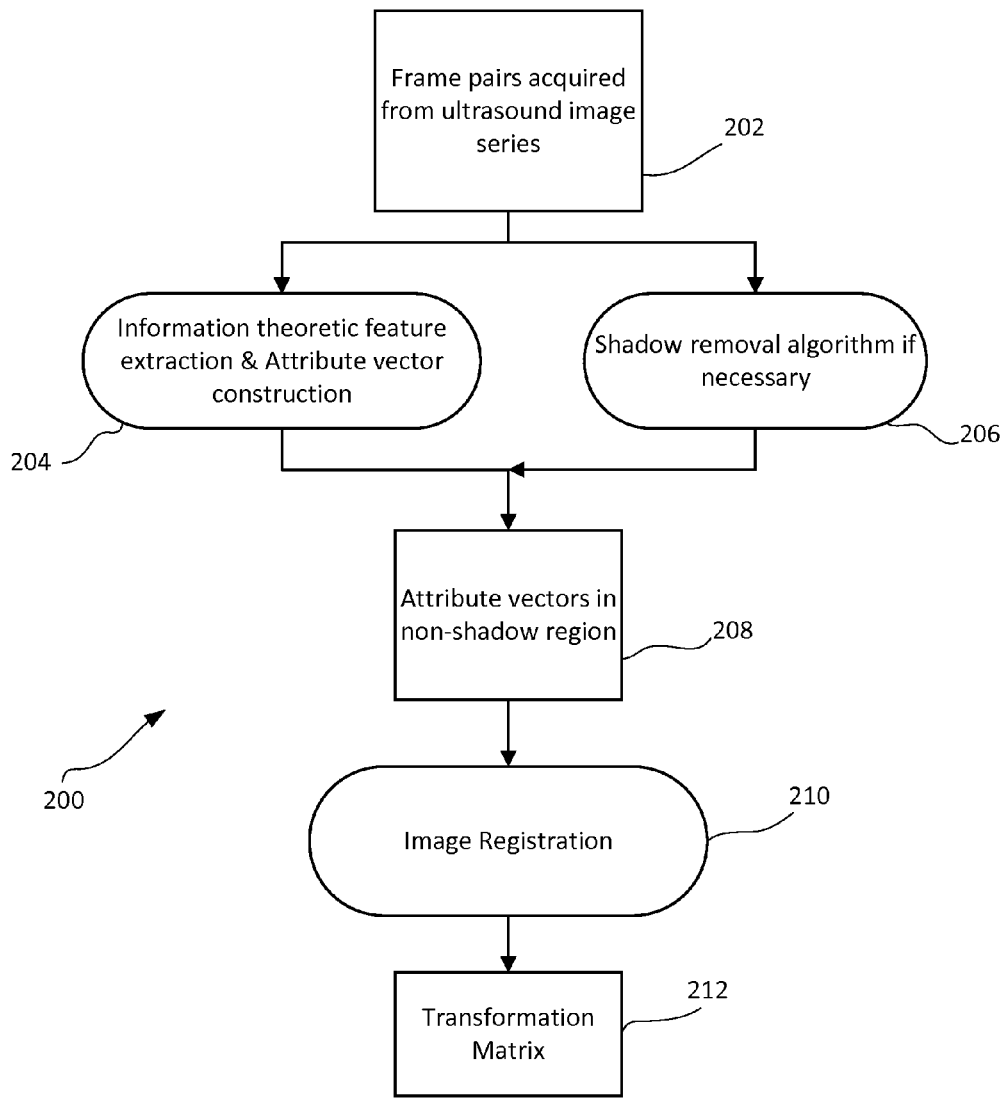
FIG. 12 illustrates an overall process for generation of the misalignment transformation

In an ultrasound image, if a point $P_0$ can be identified in 2-D frame of reference, then with the probe rotated about its axis until it is in field of view on other side (half rotation), then the axis of rotation in the plane containing the point $P_0$, point $P_0'$ and the point of intersection of normal from $P_0$ to the imaging axis can be directly computed. See, e.g., FIG. 6. Multiple image pairs can be used to find a unique transformation matrix $T_{alignment}$. FIG. 11, illustrates the transformations of FIG. 10 with the further inclusion of the alignment transformation (e.g., $T_{alignment}$). As shown, the live 2D video image and tracking information is used to compute the transformation matrix $T_{VW}$ which transforms video coordinate system into software defined world coordinate system. In addition to applying the transformation matrix $T_{VW}$ to each 2D image, the alignment transformation $T_{alignment}$ is applied to each image during the transformation into the world coordinate system. The world coordinate system is further transformed into an Image coordinate system through a fixed transformation $T_{WI}$. Thus, the video-to-world coordinate system transformation is applied after taking the alignment error into account. The alignment transformation is determined by way of registration of the mirror images acquired from a phantom with prostate model or other structures inside. However, it will be appreciated that in other embodiments that the alignment transformation could be determined using structures identified in images acquired during use. For instance, a patient prostate (or other structure) may be imaged and sets of mirror images of the prostate may be utilized to generate the alignment transformation. In any case, once the alignment transformation is determined, it may be stored and utilized for subsequent image acquisition. FIG. 12 illustrates an overall process for generation of the alignment transformation. As shown, the process 200 includes the acquisition 202 of frame pairs (e.g., 180° offset images). Features (e.g., image intensity, information theoretic feature map) from these images are extracted 204 for use in constructing attribute vectors 208. Using these attribute vectors, the image pairs are registered 210 in order to determine the transformation matrix 212 (e.g., alignment transformation).

The process further recognizes that in many ultrasound images, data exists that reduces the accuracy of the registration. For instance, most ultrasound images have shadows and speckles (e.g., artifacts) that reduce the accuracy of registration. Accordingly, the process 200 allows for optional shadow removal 206 to improve registration.

Figure 13:
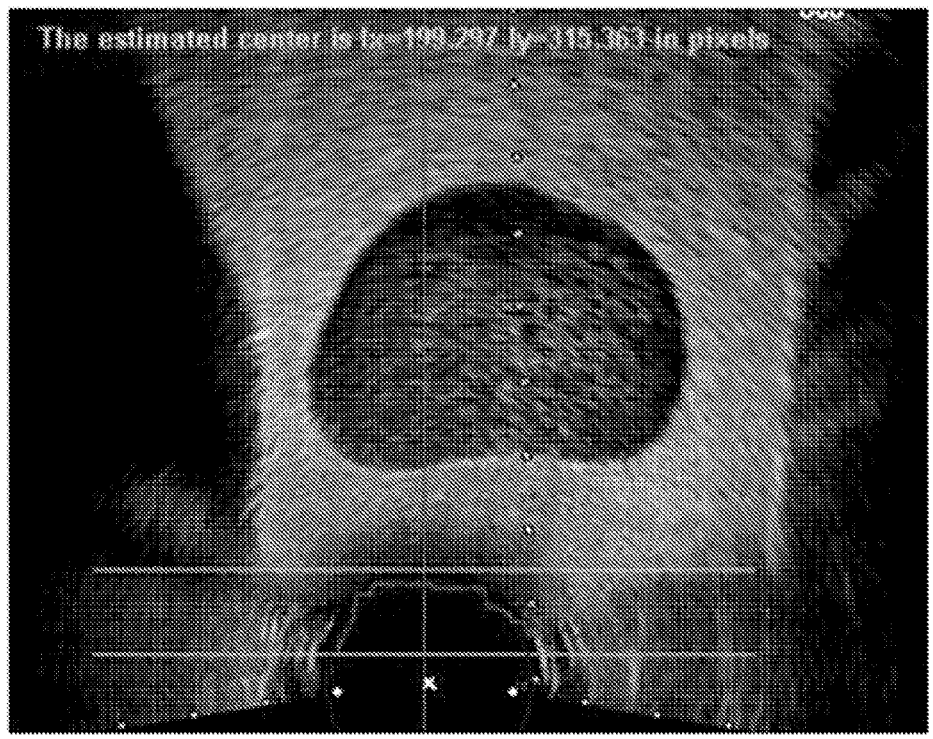
FIG. 13 illustrates the fan shape vertex detection for TRUS image.

The process utilizes a shadow removal algorithm to identify and ignore the shadows in ultrasound images. Because shadows in ultrasound images image convey no relevant information for registration, they should be removed before registration to produce better result. FIG. 13 illustrates an image plane of an ultrasound transducer. FIGS. 14A and 14B illustrate the same image plane before and after shadow removal, respectively. As shown, shadows in ultrasound images are generated along the scan line direction. It is assumed that in the region of shadow, ultrasound waves decrease in the distance in an exponential way. To find the scan lines, the vertex of the fan shape image is detected by fitting the circle of the tip boundary around the probe tip region as shown in FIG. 13. The scan lines are extracted along the diameter direction of the fan shape.

Suppose $E=\{X_1, X_2, \ldots, X_k, \ldots, X_N\}$ is the entire signal of one of the scan lines, where $X_1$ is close to the probe tip and $X_N$ is far away from the probe tip. If i is a point of that signal, then $E'=\{X_i, X_{i+1}, \ldots, X_N\}$ is a segment of that signal with mean $\mu$ and standard deviation $\sigma$. Then we can create a corresponding set of discrete points $F=\{Y_i, Y_{i+1}, \ldots, Y_N\}$ which all fall on a exponential function for k in [i,N]:

$$f(k) = A\exp(ak);$$

$$A = \mu + \frac{3}{2}\sigma;$$

$$a = \frac{1}{N}\ln(X_N/A).$$

The correlation coefficient of E' and F is calculated as:

$$\Gamma_i = \frac{\left|\frac{1}{N'}\sum_{k=i}^{N} X_k Y_k - m\right|}{\sqrt{\left|\left(\frac{1}{N'}\sum_{k=i}^{N} X_k^2 - m\right)\left(\frac{1}{N'}\sum_{k=i}^{N} Y_k^2 - m\right)\right|}};$$

$$m = \left(\frac{1}{N'}\sum_{k=i}^{N} X_k\right)\left(\frac{1}{N'}\sum_{k=i}^{N} Y_k\right).$$

Figure 14:
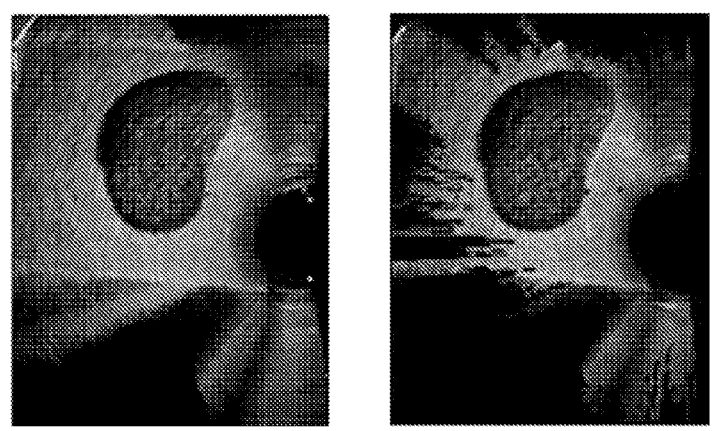
FIG. 14 illustrates the shadow removal result on TRUS image.

The shadow is detected when the point P closest to the probe tip is found where $$\sum_{1}^{P} \Gamma_i$$

is larger than the threshold T, and the segment $\{X_{Pi}, X_{P+1}, \ldots, X_N\}$ is detected as the shadow. A sample of shadow removal algorithm is shown in FIG. 14 which shows a) the original image and (b) the image after shadow removal.

Speckle noise in ultrasound images also affects the accuracy and robustness of image registration. A feature map that is not sensitive to the ultrasound speckles but sensitive to the structures of object is highly demanded for registration.

It is assumed that the distribution of the speckles from magnitude ultrasound image M(x,y) follows Rayleigh distribution:

$$p(M(x, y)) = \frac{M(x, y)}{\sigma^2} e^{-(M(x,y)^2/(2\sigma^2))}.$$

Using maximum likelihood estimation, given a region $\Omega$, the maximum likelihood estimate of $\sigma^2$ is presented as:

$$\sigma^2 = \frac{\int_\Omega M(x,y)^2 \, dx\, dy}{2\int_\Omega dx\, dy}.$$

Figure 15:
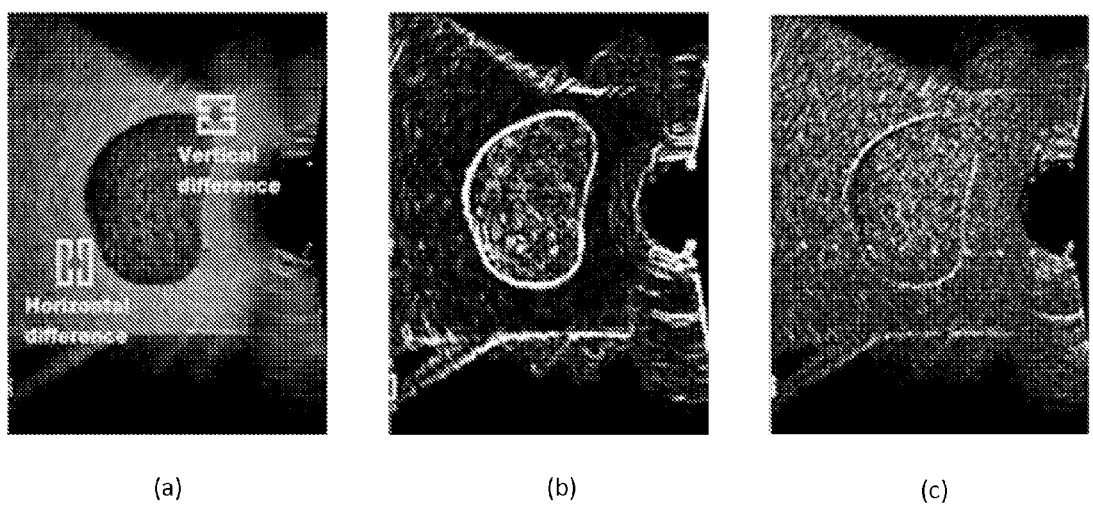
FIG. 15 compares the information theoretic feature map to gradient map of TRUS image.

Using a gradient-like operation, the relative entropy can be calculated as J for each pixel. Here $\sigma_1$ and $\sigma_2$ are calculated over two horizontal/vertical adjacent window as shown in FIG. 15a.

$$J = -1 + \frac{\sigma_1^2}{2\sigma_2^2} + \frac{\sigma_2^2}{2\sigma_1^2}.$$

The feature map is calculated by combining horizontal relative entropy $J_x$ and vertical relative entropy $J_y$.

$$F_j(x,y) = \sqrt{J_x(x,y)^2 + J_y(x,y)^2}.$$

This information theoretic feature map (FIG. 15b) is much less noisy compared to the regular gradient image (FIG. 15c) and it maintained the boundary and texture information for the prostate as is shown in FIGS. 15A-C.

For image registration, an attribute vector is constructed to combine more information for registration. In this embodiment each pixel is calculated as the image intensity and information theoretic feature at that point. To find the correspondence of the pixel ($s_1$) in a first image and ($s_2$) in a second image, the similarity of their attribute vector $Sim(s_1, s_2)$ is calculated as:

$$Sim(s_1, s_2) = \prod_i (1 - |av_i(s_1) - av_i(s_2)|)^{w_i}.$$

where $w_i$ presents the importance of the $i_{th}$ element of the attribute vector.

During the optimization process, the process searches for the transformation that derives the maximum similarity for the pixels in both images. The current method for estimation of the alignment parameters uses the Powell's algorithm to maximize the similarity. This is an algorithm for finding the local minimum of a function. The caller passes in the initial point and also a set of initial search vectors. The function is moved along the first direction to its minimum, then from there along the second direction to its minimum, and so on, cycling through the whole set of directions as many times as necessary, until the function stops decreasing. The following are the steps for Powell's algorithm:

Initialize the set of directions $u_i$ to the basis vectors,
$u_i = e_i$ i=1, ..., N
Now repeat the following sequence of steps until the function stops decreasing:
Save starting position as $P_0$.
For i=1, ..., N, move $P_{i-1}$ to the minimum along direction $u_i$ and call this point $P_i$.
For i=i=1, ..., N-1, set $u_i \rightarrow u_{i+1}$.
Set $u_N \leftarrow P_N - P_0$.
Move $P_N$ to the minimum along direction $u_N$ and call this point $P_0$.

The above noted processes allow for improving the registration between image pairs and thereby improving the calculation of the alignment transformation.

In addition to recognizing that misalignments between a probe and tracker assembly need to be corrected to allow for improved image registration, the inventors have also recognized that other relative motion may be present between images and that correction of this intra-image motion is desirable for improved image registration. That is, perceived misalignment in a reconstructed image may not happen only due to misalignment of the 2D transducer from a known position/axis, it may also happen due to shift in gland or object being imaged as a result of pressure of the transducer or other instrument. Further, misalignment may also happen as a result motion of the object relative to the imaging plane due to breathing or patient movement. As an example, prostate gland can be imaged by inserting ultrasound transducer transrectally. The transducer is pressed against rectal wall to get better imaging. This pressure often deforms the gland and the rotation or motion of transducer for image acquisition may cause gland to roll to a side and back, resulting in reconstruction artifacts similar to misalignment. To account for this motion an image registration based method for performing correction of the reconstructed image after they are acquired is presented.

Figure 16:
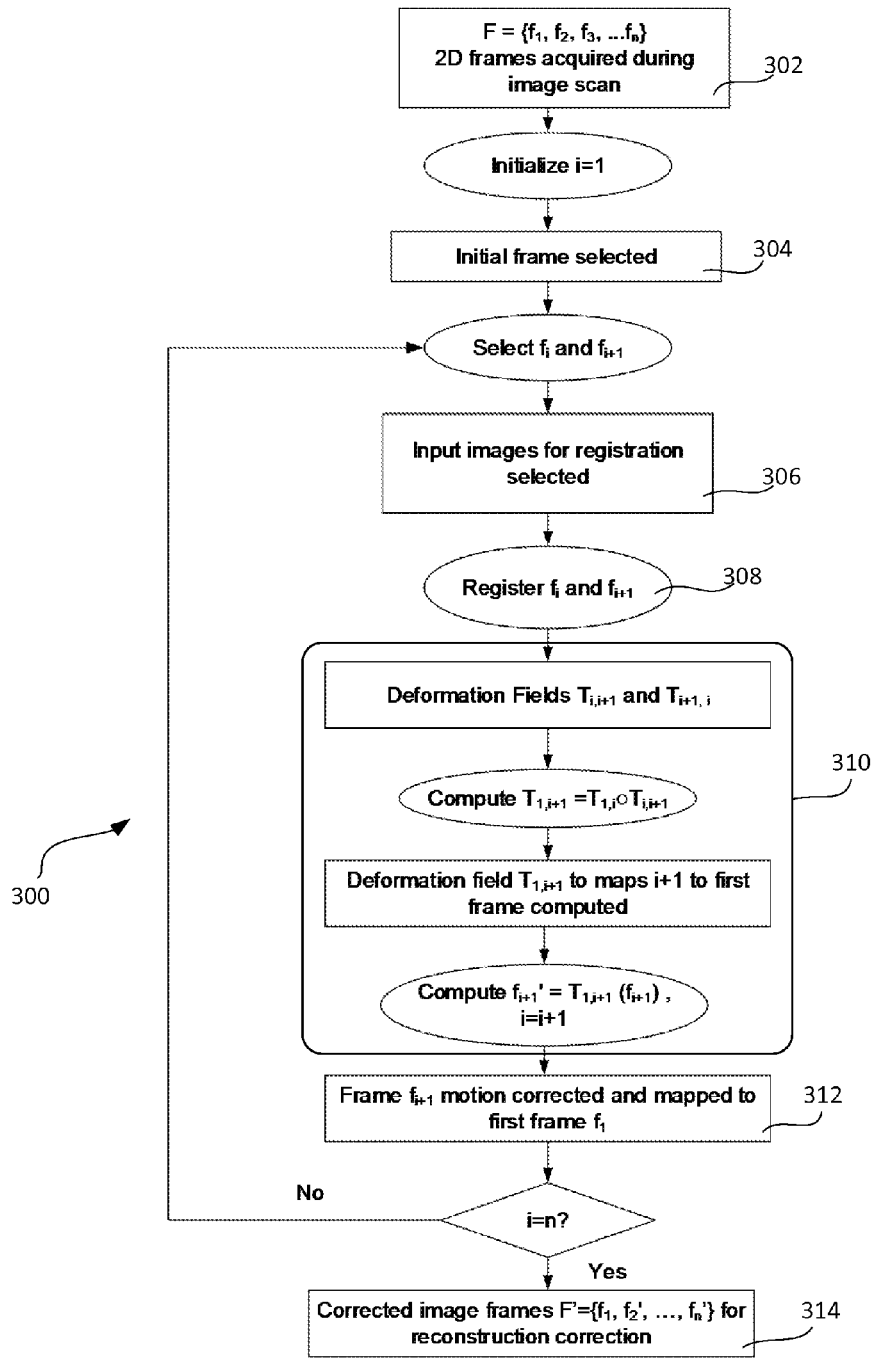
FIG. 16 illustrates image registration based reconstruction correction method.

In a reconstructed image, assuming a fine enough resolution, the consecutive raw images will be very "close" to each other, i.e., the motion artifacts between consecutive slices will be minimal while the mutual information will also be very high. This helps in correcting for small motions in consecutive slices. In the presented process 300 shown in FIG. 16, images are acquired 302 and an initial frame is selected 304 and then each pair of consecutive images/frames is selected 306 and these frames are registered 308 (say, (i+1)-th) such that the motion between consecutive frames can be computed 310 as transformation $T_{i+1,i}$, where $T_{i,j}$ maps image j into frame of reference of image i. The motion correction matrix $T_{i,i+1}$ can thus be computed as inverse of $T_{i+1,i}$ and applied on the 312 the (i+1)-th frame such that it maps (i+1)-th frame into frame of reference of i-th frame. Starting with the first image, as a result of concatenation of transformations, all image frames will be mapped back to frame of reference of the first image frame, i.e., $T_{1,i+1} = T_{1,2} \circ T_{2,3} \circ \ldots T_{i,i+1}$. Note that the choice of first image is arbitrary and any image can be chosen as reference if cyclic boundary conditions are used. Likewise, a central image may be registered to both, previous and next consecutive image to make method more robust. After all images are registered, they can be placed in a common frame of reference thus removing the motion artifacts from the reconstructed image 314. The resulting reconstructed 3D image may then be let put to a display and utilized for guidance during a medical procedure.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in similar or other embodiments and with various modifications required by the particular application(s) or use(s) of the present invention. It is intended that the appended claims be construed to include alternative embodiments to the extent permitted by the prior art.

What is claimed:

1. A method for calibrating images obtained from an ultrasound imaging device where the imaging device is supported by a positioning mechanism, comprising:
obtaining at least first and second images from an ultrasound imaging device while said positioning device supports the ultrasound imaging device in first and second positions, respectively, wherein the first and second of images are obtained through rotation of said ultrasound imaging device about an axis of rotation wherein the first and second images are mirror images acquired at angles 180 degrees apart, wherein said positioning mechanism is designed to limit movement of said ultrasound imaging device to said axis of rotation between said first and second positions;

identifying a first distance between said an object in said first image and a known reference point in said first image;

identifying a second distance between said object in said second image and the known reference point in the second image;

determining a difference in said first and second distances; and calculating a transformation, based on said differences of said first and second images, wherein said transformation defines a calibration of offsets between said reference point of said ultrasound images and said axis of movement of said positioning mechanism.

2. The method of claim 1, further comprising:
acquiring a sequence of two-dimensional (2D) images of an anatomical object using said ultrasound imaging device as supported by said positioning mechanism, wherein said 2D images are acquired at different positions about said axis of movement; and applying said transformation to each of said sequence of 2D images, wherein said transformation places said 2D images in a common frame of reference to define a sequence of corrected 2D images.

3. The method of claim 2, wherein:
said obtaining at least first and second images and calculating said transformation is performed during a common procedure while acquiring said sequence of images.

4. The method of claim 3, wherein said first and second images are part of said sequence of images.

5. The method of claim 2, further comprising:
reconstruct said sequence of corrected 2D images to generate a 3D image of said anatomical object.

6. The method of claim 5, wherein said transformation updates the correlation between real world and image frames during a medical procedure, wherein said medical procedure is performed under 3D image guidance.

7. The method of claim 5, wherein registering said sequence of 2D images provides real world to image space calibration.

8. The method of claim 2, further comprising:
preprocessing said sequence of 2D images to remove at least one of speckle and shadow.

9. The method of claim 2, wherein said image reference point comprises an image axis, wherein said transformation accounts for offsets between said image axis and said axis of movement.

10. The method of claim 2, wherein said positioning mechanism moves said ultrasound imaging device about a rotational axis of movement.

11. The method of claim 2, wherein said positioning mechanism moves said ultrasound imaging device about a linear axis of movement.

12. The method of claim 2, wherein said sequence of two-dimensional (2D) images are acquired from one of a side fire ultrasound transducer and an end-fire ultrasound transducer.

13. The method of claim 1 wherein said transformation defines in-plane calibration values.

14. The method of claim 1, wherein a plurality of pairs of images are obtained through rotation of said ultrasound imaging device about said axis of rotation such that each pair of images are mirror images acquired at angles 180 degrees apart.

15. The method of claim 1, wherein the movement of the ultrasound imaging device is non-uniform.

16. A method for calibrating images obtained from an ultrasound imaging device where the imaging device is supported by a positioning mechanism, comprising:
obtaining at least first and second two dimensional (2D) images from an imaging device while said positioning device supports the ultrasound imaging device in first and second angular positions at angles 180 degrees apart, respectively, wherein said positioning mechanism is designed to limit movement of said ultrasound imaging device to a rotational axis of movement between said first and second angular positions;

identifying a first distance between an object in said first image and an imaging axis of said first 2D ultrasound image;

identifying a second distance between said object in said second image and the imaging axis of said second 2D ultrasound image;

determining a difference in said first and second distances; and calculating a transformation, based on said difference, wherein said transformation defines a calibration of offsets between said imaging axis of said 2D ultrasound images and said rotational axis of said positioning mechanism.

17. The method of claim 16, wherein obtaining comprises obtaining a plurality of pairs of 2D ultrasound images where each pair of images are 180 degrees apart.

18. The method of claim 17, further comprising;
identifying first and second distances between an object in each pair of images and said imaging axis of each image;
determining differences between said first and second distances of each pair of images;
calculating said transformation, based on said differences.

19. The method of claim 18, further comprising:
acquiring a sequence of two-dimensional (2D) images of an anatomical object using said ultrasound imaging device as supported by said positioning mechanism, wherein said 2D images are acquired at different positions about said axis of movement; and applying said transformation to each of said sequence of 2D images, wherein said transformation places said 2D images in a common frame of reference to define a sequence of corrected 2D images.

20. The method of claim 19, further comprising:
reconstruct said sequence of corrected 2D images to generate a 3D image of said anatomical object.

21. A system for use in obtaining and calibrating images obtained from an ultrasound imaging device supported by a positioning mechanism, comprising:
an ultrasound imaging probe operative to obtain two-dimensional (2D) ultrasound images;

a positioning mechanism adapted to support said ultrasound imaging probe and move said ultrasound imaging probe between first and second mirror positions at angles 180 degrees apart, wherein said positioning mechanism limits movement of said probe to a single degree of freedom relative to a rotational axis;

a processor operative to:
- receive first and second 2D ultrasound images from said ultrasound imaging device at said first and second mirror positions,
- identify a first distance between an object in said first 2D ultrasound image and an imaging axis of said first 2D ultrasound image;
- identify a second distance between said object in said second 2D ultrasound image and the imaging axis of said second 2D ultrasound image; and
- calculate a transformation, based on differences in said first and second distances, wherein said transformation defines a calibration of offsets between said imaging axis of said first and second 2D ultrasound images and said rotational axis of said positioning mechanism.

22. The system of claim 21, wherein said processor if further operative to:
- receive a sequence of two-dimensional (2D) images of an anatomical object from said ultrasound imaging device as supported by said positioning mechanism, wherein said 2D images are acquired at different positions relative to said movement axis;
- apply said transformation to each of said sequence of 2D ultrasound images, wherein said transformation places said 2D images in a common frame of reference to define a sequence of corrected 2D images; and
- reconstruct said sequence of corrected 2D images to generate a 3D image of said anatomical object.

23. The system of claim 22, further comprising:
a monitor operative to output said 3D image.

* * * * *

UNITED STATES PATENT AND TRADEMARK OFFICE
CERTIFICATE OF CORRECTION

PATENT NO. : 9,131,922 B2
APPLICATION NO. : 13/752831
DATED : September 15, 2015
INVENTOR(S) : Xin Li and Ramkrishnan Narayanan Page 1 of 1

It is certified that error appears in the above-identified patent and that said Letters Patent is hereby corrected as shown below:

In the claims

Column 17, line 17, delete "if" and insert therefor --is--.

Signed and Sealed this
Twenty-second Day of March, 2016

Michelle K. Lee
*Director of the United States Patent and Trademark Office*